United States Patent
Budmiger

[11] 4,071,912
[45] Feb. 7, 1978

[54] LIGHT FILTER FOR WELDER'S MASK

[75] Inventor: Hermann Budmiger, Seewen, Solothurn, Switzerland

[73] Assignee: Revue Thommen AG, Waldenburg, Switzerland

[21] Appl. No.: 637,000

[22] Filed: Dec. 2, 1975

[30] Foreign Application Priority Data

Dec. 2, 1974 Switzerland .................. 16064/74
July 14, 1975 Switzerland .................. 9265/75

[51] Int. Cl.² .............................................. A61F 9/06
[52] U.S. Cl. ............................................. 2/8; 350/150; 350/352; 350/356
[58] Field of Search ............... 2/8, 14 J, 14 H, 2, 2/431, 432; 350/150, 160 P, 160 LC; 200/61.01

[56] References Cited
U.S. PATENT DOCUMENTS

| | | | |
|---|---|---|---|
| 3,737,211 | 6/1973 | Cutchen et al. | 350/150 X |
| 3,756,692 | 9/1973 | Scott | 2/14 J X |
| 3,785,721 | 1/1974 | Harsch | 350/150 |
| 3,827,000 | 7/1974 | Matsushita et al. | 350/150 X |
| 3,873,804 | 3/1975 | Gordon | 2/8 X |
| 3,943,573 | 3/1976 | Budmiger | 2/8 |

*Primary Examiner*—Werner H. Schroeder
*Assistant Examiner*—Peter Nerbun
*Attorney, Agent, or Firm*—Karl F. Ross

[57] ABSTRACT

A welder's mask has a lens at least part of which is formed of an infrared filter, an ultaviolet filter, a polarizer, an analyzer, and an optoelectric element between the polarizer and analyzer. The optoelectric element may be a ceramic crystal or fluid crystal that is electrically energizable by means of automatic circuitry connected to an UV-sensitive photocell to rotate the polarization plane of light coming from the polarizer to the analyzer in order automatically to darken the lens when exposed to a welding flame or arc.

1 Claim, 8 Drawing Figures

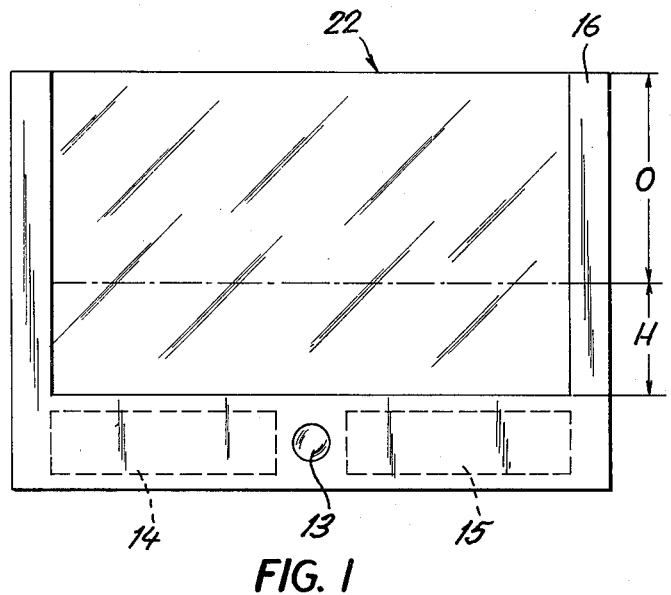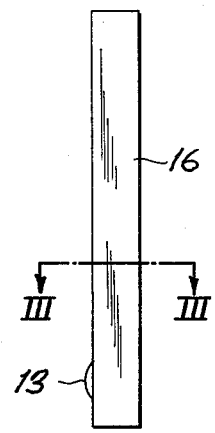
FIG. 1  FIG. 2
FIG. 3
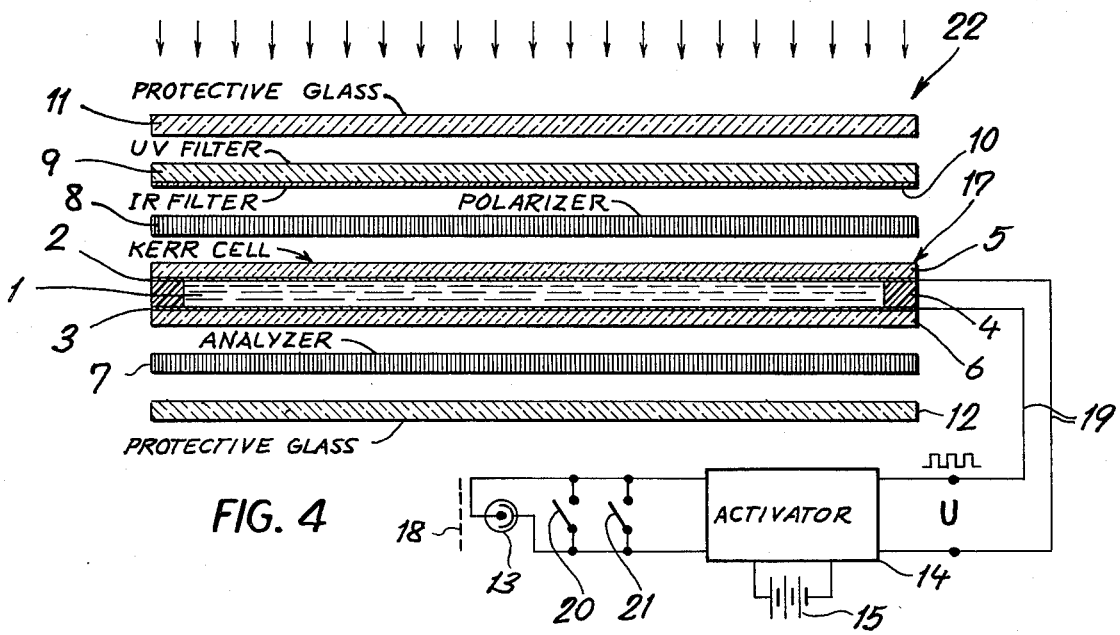
FIG. 4

LIGHT FILTER FOR WELDER'S MASK

FIELD OF THE INVENTION

The present invention relates to a light-filtering device. More particularly this invention concerns a lens arrangement usable in goggles or a helmet for a welder.

BACKGROUND OF THE INVENTION

Gas and electric-arc welding produces an extremely bright light that is rich in ultraviolet and infrared rays. Frequent or prolonged exposure to such light can blind a person. For this reason a helmet or goggles are usually worn by a welder, with a lens in the helmet or goggles provided with filters that stop the infrared and ultraviolet rays.

The principal difficulty with such a light-filtering lens or device is that visible light is also greatly attenuated. Thus it is customary for the welder to strike the arc or stop the welding operation with the goggles or helmet tilted up so that he can see what he is doing, and thereafter to put the goggles or helmet in place, as the light generated by the welding operation is thereafter then sufficient to allow him to see his work. This short but frequent exposure to the unfiltered light from the arc or flame is in the long run very harmful.

OBJECTS OF THE INVENTION

It is therefore an object of the present invention to provide an improved eyeshield for protecting the eyes of a welder or the like.

Another object is the provision of a light-filtering device which normally allows most of the available light to pass through but which darkens when exposed to the powerful light of a welding flame or arc.

Yet another object is the provision of such a device which functions automatically to protect the eyes of the welder.

SUMMARY OF THE INVENTION

These objects are attained according to the present invention in a light-filtering device which has an ultraviolet filter and an infrared filter in line with each other. In addition a polarizer and an analyzer are stacked with the filters one behind the other with an optoelectric element sandwiched between the polarizer and analyzer for rotating the plane of polarization of light passing backwardly from the polarizer toward the analyzer. Means is provided for sensing the strong light rays emitted by a welding flame or arc and for automatically energizing the optoelectric element so as to greatly reduce light flow through the filtering device.

The light-attenuating device in the light-filtering arrangement according to the present invention uses two polarizers and an optoelectric element. Light waves are known to be transverse waves with a plurality of oscillations aligned in various direction at right angles to the propagation direction. A polarizer only passes waves having a predetermined oscillation direction. Crossed polarizers pass, depending on the angular orientation they have relative to one another, more or less light. When the crossing angle is 90° no light at all can pass through. The second polarizer, the one in back of the first polarizer, is usually referred to as the analyzer.

In accordance with this invention an optoelectric element is placed between the polarizer and the analyzer so that the polarized light passing backwardly from the polarizer has its plane twisted somewhat before it reaches the analyzer. Thus if the polarizer and analyzer are crossed at 90° relative to one another no light goes through. When the optoelectric element is energized light will be let through the stack if the element is set to rotate the light from the polarizer through 90° before letting it through to the analyzer. The opposite effect may also be achieved by aligning the polarizer and analyzer so as normally to pass all light and using the optoelectric element between them to decrease the amount of light that can pass through the stack.

The optoelectric element of such a kerr cell may be a so-called fluid crystal or transparent ceramic cell.

In accordance with further features of this invention I provide electric circuitry including a photocell which responds only to ultraviolet light an is connected to the electrodes of the electrically energizable optoelectric element between the polarizer and analyzer. When exposed to a bright light as is typically only produced by a welding operation, the photocell immediately energizes the optoelectric element through an appropriate amplifying circuit to modify the transparency of the filter stack. In the device defined in the appended claims, a manually operated or acoustically operated switch operates to reduce the transparency of the lens in accordance with this invention.

BRIEF DESCRIPTION OF THE DRAWING

FIG. 1 is a front view of a light-filtering device in accordance with this invention, FIG. 2 is a side view of the device shown in FIG. 1, FIG. 3 is a section taken along lines III—III of FIG. 2, FIG. 4 is an exploded view of the lens in accordance with this invention.

SPECIFIC DESCRIPTION

Figure 5:
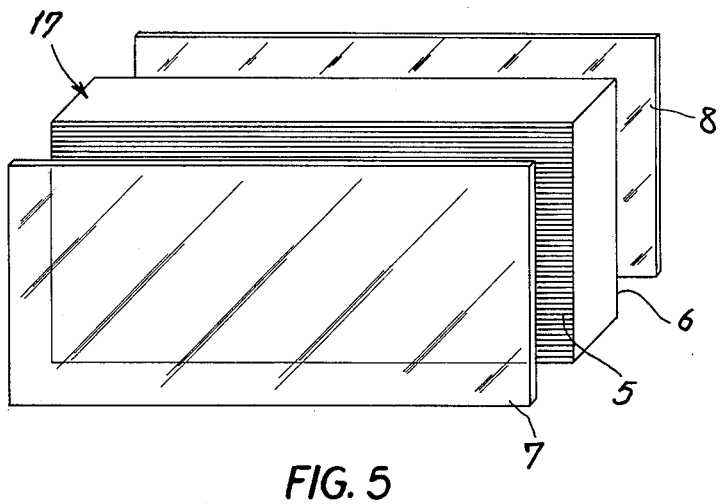
FIGS. 5 and 6 are perspective exploded views illustrating operation of the lens device of the present invention.

FIGS. 1, 2 and 3 show a light-filtering arrangement in accordance with this invention intended for use as the lens of goggles or in a helmet for a welder. Such an arrangement has a headpiece frame 16 fitted with a lens 22 having an upper part O which is constituted as a standard welder's lens with a strong filter for ultraviolet light and a similarly strong filter for infrared light so that this upper portion O always heavily attenuates light in the visible spectrum also. The lens 22 has a lower portion H which is formed in accordance with this invention and described below. In addition the frame 16 carries a photocell 13, a control circuit 14 connected to the photocell 13, and a battery 15.

FIG. 4 shows the structure of the lower portion of the lens 22 in greater detail. Thus the lower portion H of the filter 22 has an outer protective glass 11 on which light falls as indicated by the arrows. Behind this protective glass 11 there is provided an ultraviolet filter 9 on whose back face is provided an infrared filter layer 10. In back of this element there is a light polarizer 8 and then an optoelectric element 17. An analyzer 7, which is simply another polarizer, is provided behind the element 17 and behind this is provided another protective glass 12.

The optoelectric element 17 comprises a pair of transparent glass plates 5 and 6 provided with transparent electrically conductive electrode layers 2 and 3. A fluid crystal 1, such as nitrobenzene, is provided between the electrodes 2 and 3, and a spacer 4 holds the plates 5 and 6 apart by a distance of between 10 microns and 30 microns. The edge of the optoelectric element or kerr cell 17 is sealed. See *Fundamentals of Optics* by Jenkins and White (McGraw-Hill: 1957) at pages 502ff for a discussion of polarizers and analyzers and at pages 390ff for a discussion of the function of a kerr cell.

Figure 6:
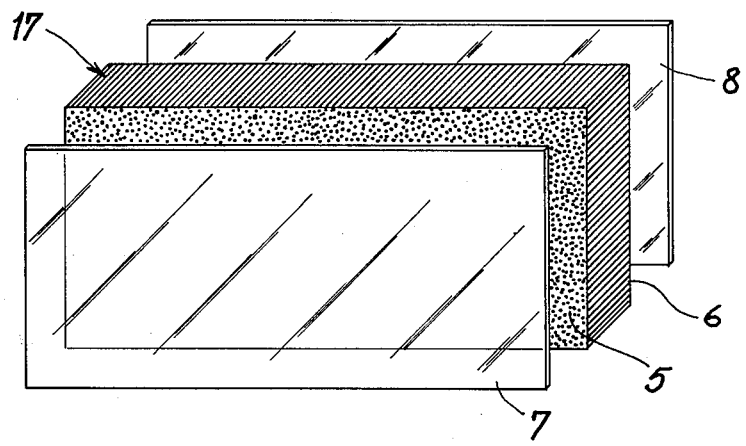

The molecular structure of the fluid crystal is such that an electric field orients the molecule in a predetermined direction. FIGS. 5 and 6 illustrate this. In FIG. 5 the molecules are oriented parallel to the faces of the cell, that is transverse to the light direction. When as shown in FIG. 6 the electrodes 5 and 6 are energized, the molecules arrange themselves perpendicular to the surfaces of the crystal. In FIGS. 5 and 6 the polarizer and the analyzer are arranged so that they normally allow light to pass through them.

When as shown in FIG. 6 the kerr cell 17 is energized, light passing through the polarizer 8 has its polarization plane rotated so that much of it is blocked by the analyzer 7. Thus in this arrangement the device darkens when energized.

This is effected by use of the actuator circuit shown in FIG. 4 wherein an activator 14 powered by a battery 15 can produce an output current U that it feeds through lines 19 to the electrode layers 2 and 3. The photocell 13 is connected to the input of this activator and is itself provided with a filter 18 that only allows ultraviolet light to irradiate it. The activator 14 when energized by the cell 13, by manual switch 20 or by a sound-operated switch 21, produces a square-wave alternating-current signal between 1 and 6 volts at a frequency of 50 Hz. The cell 17 is switched from the condition of FIG. 5 to the condition of FIG. 6 with a voltage of 1 volt so that when a strong ultraviolet light falls on the cell 13 or the switch 21 detects a loud noise such as the striking of an arc, the activator will energize the cell 17 through the lines 19 and cause the normally transparent light-filter arrangement to attenuate light passing through it.

The battery 15 is a standard transistor-type 9-volt battery. The device with such an arrangement is capable of reacting and darkening in a fraction of a second. In addition the switch 20 may be manually operated to darken the lens or the switch 21 acoustically operated if desired to override the automatic actuation of the device. Such an arrangement has been found to be highly effective in protecting the eyes of the welder who is able to look through the lower portion H as he or she strikes an arc or lights the torch and thereafter can use the lens 22 as a normal welding lens as it will be entirely dark. This arrangement satisfies the DIN 46 47 standard as well as ISO norms for windows in welders' eyeshields.

It is also possible to use the device in reverse, that is have it normally dark and energize the cell 17 to make the arrangement transparent. It has been found that the time to darken the arrangement is longer in this case but that thus it is possible to achieve a greater darkening. It is also possible in accordance with this invention to provide a plurality of such kerr cells in order to increase the light attenuation of the unit.

Figure 8:
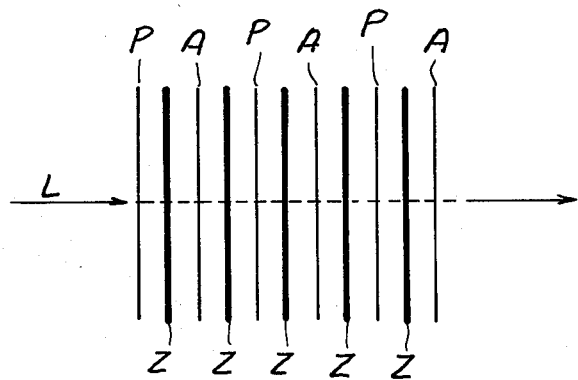
FIG. 8 is a side diagrammatic view illustrating another arrangement in accordance with the present invention operating along principles illustrated in FIG. 7.

A very strong light attenuation is possible with the arrangement of FIG. 8. This operates with a fluid crystal having a transparent ceramic cell Z. An advantage of such an arrangement is that several different transmission levels can be achieved by energizing selectively only one or more of the cells.

Figure 7:
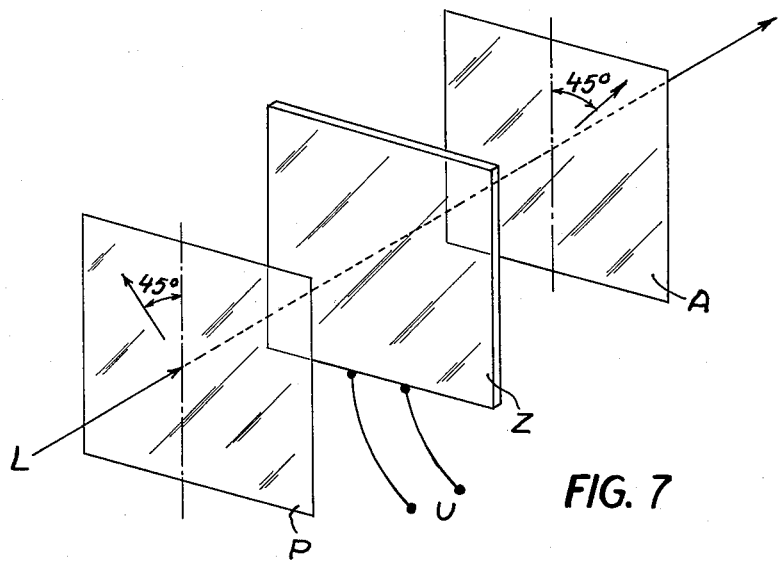
FIG. 7 is a perspective exploded view showing another arrangement in accordance with this invention.

FIG. 7 illustrates the operation of this arrangement. Thus a polarizer P, an analyzer A, and a ceramic cell Z are employed. The polarizer P only passes light waves whose plane of polarization is tipped 45° toward the left, and the analyzer A only passes light waves which are polarized in a plane tipped 45° to the right. Thus so long as the ceramic cell Z is not excited no light L passes.

When the voltage U is applied to this cell Z it becomes double refractive and light is passed by the assembly. If the polarization directions are not tipped by 90° relative to one another, only a predetermined amount of light is passed through according to the amount of voltage applied across the cell.

FIG. 8 shows five such arrangements lying one behind the other. In this arrangement each polarizer works as the analyzer for a preceding polarizer and vice versa. Thus according to the selective operation of the various cells Z it is possible to achieve a different light attenuation according to need. It is also possible to use kerr cells of the fluid-crystal type in the place of the ceramic cells Z of FIG. 8.

I claim:
1. A welder's eyeshield comprising:
a headpiece;
a window on said headpiece alignable with the eyes of a person wearing same;
an infrared filter in said window;
an ultraviolet filter in said window in line with said infrared filter;
a polarizer in said window in line with said filters;
an analyzer in said window in line with and behind said polarizer;
means including an optoelectric element in said window between said polarizer and said analyzer electrically energizable for rotating the plane of polarization of light passing from said polarizer toward said analyzer;
a photocell on said headpiece for generating an output on detection of strong ultraviolet radiation;
an acoustical device on said headpiece responsive to sound;
circuit means between said element and said photocell for operating same to reduce light passage through said window on generation of said output, said circuit means including means responsive to said acoustic device for operating said element to reduce light passage through said window upon detection of a sound by said device attributable to the striking of a welding arc; and
a battery on said headpiece for powering said circuit means.

* * * * *